(12) United States Patent
Hua et al.

(10) Patent No.: US 8,974,769 B2
(45) Date of Patent: *Mar. 10, 2015

(54) MAGNETIC NANOCOMPOSITE WITH MULTI-BIOFUNCTIONAL GROUPS AND METHOD FOR FABRICATING THE SAME

(75) Inventors: Mu-Yi Hua, Tao-Yuan (TW); Hung-Wei Yang, Tao-Yuan (TW); Rung-Ywan Tsai, Kaohsiung (TW); Kuo-Chen Wei, Taipei (TW); Pin-Yuan Chen, Taipei (TW); Hao-Li Liu, Tao-Yuan (TW)

(73) Assignee: Chang Gung University, Kwei-Shan, Tao-Yuan (TW)

( * ) Notice: Subject to any disclaimer, the term of this patent is extended or adjusted under 35 U.S.C. 154(b) by 739 days.

This patent is subject to a terminal disclaimer.

(21) Appl. No.: 12/799,893

(22) Filed: May 4, 2010

(65) Prior Publication Data

US 2011/0104077 A1    May 5, 2011

(30) Foreign Application Priority Data

Nov. 2, 2009 (TW) ................................ 98137282 A (51) Int. Cl.
| | | |
|---|---|---|
| *A61K 49/18* | (2006.01) | |
| *A61K 47/34* | (2006.01) | |
| *A61K 9/50* | (2006.01) | |
| *A61K 31/785* | (2006.01) | |
| *A61K 47/48* | (2006.01) | |
| *B82Y 5/00* | (2011.01) | |

(52) U.S. Cl.
CPC ....... *A61K 47/48661* (2013.01); *A61K 49/1857* (2013.01); *B82Y 5/00* (2013.01); *Y10S 977/892* (2013.01)
USPC ..................... 424/9.323; 424/497; 424/78.08; 514/769; 977/892

(58) Field of Classification Search
CPC .................... A61K 47/48861; A61K 49/1857; B82Y 5/00
See application file for complete search history.

(56) References Cited

U.S. PATENT DOCUMENTS

2007/0029195 A1* 2/2007 Li et al. .................... 204/403.01
2008/0314766 A1* 12/2008 Alocilja et al. ............ 205/777.5
2009/0123939 A1* 5/2009 Alocilja et al. ................ 435/7.2

OTHER PUBLICATIONS

Lu, et al., "Aniline dimer-COOH assisted preparation of well-dispersed polyaniline-Fe3O4 nanoparticles", 2005, Nanotechnology, 16, pp. 1660-1665.*
Huang, L., et al., "Synthesis and characterization of electroactive and biodegradable ABA block copolymer of polylactide and aniline pentamer", 2007, Biomaterials, 28, pp. 1741-1751.*
Hu, J., et al., "A New Oxidation State of Aniline Pentamer Observed in Water-Soluble Electroactive Oligoaniline-Chitosan Polymer", 2007, J. Polymer, Sci., A., 46, pp. 1124-1135.*
Yang et al., "A new drug of BCNU bound on magnetic nano-particles and their in vitro antitumor activity against Glioma C6 cells," 2009 IEEE International Magnetics Conference, May 4-8, 2009.

* cited by examiner

*Primary Examiner* — Michael G Hartley
*Assistant Examiner* — Lance Rider
(74) *Attorney, Agent, or Firm* — Muncy, Geissler, Olds & Lowe, P.C.

(57) ABSTRACT

The present invention proposes a magnetic nanocomposite with multi-biofunctional groups, which comprises a core and a shell wrapping the core, wherein the core contains magnetic nanoparticles, and wherein the shell is made of a conductive polymer with multi-biofunctional groups where a medicine, an antibody or a fluorescent label can be attached.

24 Claims, 8 Drawing Sheets
(6 of 8 Drawing Sheet(s) Filed in Color)

MAGNETIC NANOCOMPOSITE WITH MULTI-BIOFUNCTIONAL GROUPS AND METHOD FOR FABRICATING THE SAME

BACKGROUND OF THE INVENTION

1. Field of the Invention

The present invention relates to a magnetic nanocomposite and a method for fabricating the same, particularly to a magnetic nanocomposite with multi-biofunctional groups and a method for fabricating the same.

2. Description of the Related Art

As a single-component nanoparticle is less likely to accomplish various novel applications, many researchers have been devoted to the development and application of multi-component and multi-functional nanocomposites in recent years. Novel functions of a nanoparticle can be achieved via integrating the nanoparticle and another material. In general, multi-component nanocomposites may be categorized into core-shell nanoparticles and hybrid nanocomposite particles. A hybrid nanocomposite particle refers to a nanoparticle containing at least two components homogenously distributed in the nanoparticle. The core-shell nanoparticles include core-shell nanocomposite colloids and hollow spheres. The properties of the materials of the core and shell will influence the overall physical and chemical characteristics of the nanoparticle, such as catalytic activity, reactivity, selectivity, solubility and biocompatibility.

In the field of medicine and inspection, attention is usually paid to magnetic nanocomposites. Magnetic nanocomposites are primarily used in MRI (Magnetic Resonance Imaging) contrast agents and the medicine carriers. Most of the current contrast agents have a core-shell structure, wherein a polymeric shell envelops a ferric-oxide ($Fe_2O_3$) or ferric ferrous-oxide ($Fe_3O_4$) core. The core-shell nanoparticle has a size of about 10-30 nm. There is also a microbubble-type contrast agent, wherein the core is a bubble and the shell is made of PVA containing magnetic particles. Such a microbubble can function as the contrast agents of MRI and ultrasonic imaging. However, the microbubble has too large a size about 3.89 μm. In the conventional technology, the fabrication process of the abovementioned magnetic nanoparticles for MRI is complicated and time-consuming and even needs crosslinkers or enveloping agents. Thus, the conventional magnetic nanoparticles are more biotoxic and hard to purify. Further, the conventional magnetic nanoparticles are still insufficient in performance.

Accordingly, the present invention proposes a novel magnetic nanocomposite with multi-biofunctional groups, which can effectively overcome the abovementioned problems, and which can function as an MRI contrast agent and a medicine carrier.

SUMMARY OF THE INVENTION

The primary objective of the present invention is to provide a magnetic nanocomposite with multi-biofunctional groups and a method for fabricating the same, wherein the method of the present invention can fabricate a magnetic nanocomposite in a simple, fast and low-cost way, wherein the magnetic nanocomposite has a shell made of a conductive polymer with multi-biofunctional groups and a core containing a superparamagnetic nanoparticle.

Another objective of the present invention is to provide a magnetic nanocomposite with multi-biofunctional groups and a method for fabricating the same, wherein the magnetic nanocomposite can be attached to by a fluorescent label or a special antibody to function as an intelligent MRI contrast agent or a medicine carrier.

A further objective of the present invention is to provide a magnetic nanocomposite with multi-biofunctional groups and a method for fabricating the same, wherein the fabrication is exempt from surfactants, dispersants and crosslinkers, wherefore the biotoxicity of the nanocomposite of the present invention is lower than that of the conventional nanocomposite.

To achieve the abovementioned objectives, the present invention proposes a magnetic nanocomposite with multi-biofunctional groups, which comprises a core and a shell wrapping the core, wherein the core contains magnetic nanoparticles, and wherein the shell is made of a conductive polymer with multi-biofunctional groups.

The present invention also proposes a method for fabricating the abovementioned magnetic nanocomposite, which comprises steps: uniformly agitating a first mixture liquid containing ferric ion and ferrous ion, and adding a basic solution into the first mixture liquid to form a second mixture liquid containing a plurality of magnetic nanoparticles; separating the magnetic nanoparticles from the second mixture liquid; and uniformly mixing the magnetic nanoparticles with a biocompatible water-soluble self-acid-doped polyaniline derivative to form a third mixture liquid, using an acidic solution to modify the third mixture liquid to have a pH value of 4-5, oscillating the third mixture liquid to enable a reaction generating a plurality of magnetic nanocomposites, and separating the magnetic nanocomposites from the third mixture liquid to obtain magnetic nanocomposites with multi-biofunctional groups.

Below, the embodiments are described in detail to make easily understood the objectives, technical contents, characteristics and accomplishments of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The present invention is to provide a novel magnetic nanocomposite with multi-biofunctional groups and a method for fabricating the same. The magnetic nanocomposite of the present invention comprises a magnetic nanoparticle; and a conductive polymer wrapping the magnetic nanoparticle and having multi-biofunctional groups. Because of magnetism, the magnetic nanocomposites can function as an MRI contrast agent or a tracer. Because of the multi-biofunctional groups, the magnetic nanocomposites can be attached to by a fluorescent label or an antibody to function as an intelligent MRI contrast agent or a medicine carrier. The method of the present invention can fabricate a multi-biofunctional group-containing magnetic nanocomposite in a simple way without using any surfactant or dispersant. The multi-biofunctional group-containing magnetic nanocomposites of the present invention can easily disperse in water and have low biotoxicity and a simple purification process.

Figure 1:
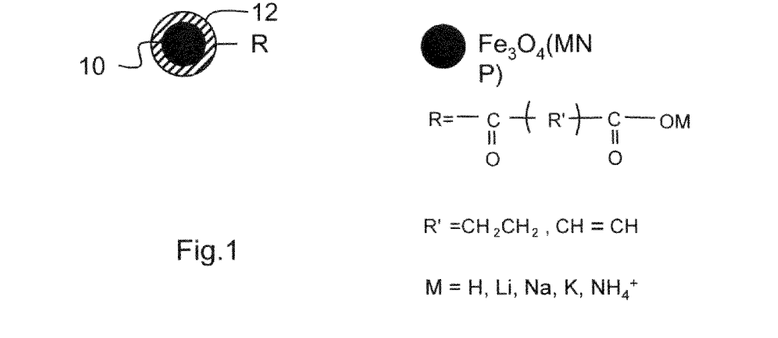
FIG. 1 is a diagram schematically showing the structure of a magnetic nanocomposite with multi-biofunctional groups according to the present invention.

Refer to FIG. 1 a diagram schematically showing the structure of a magnetic nanocomposite with multi-biofunctional groups according to the present invention. The magnetic nanocomposite of the present invention can function as an intelligent contrast agent and comprises a core 10 and a shell 12 wrapping the core 10, wherein the core 10 contains superparamagnetic nanoparticles, and wherein the superparamagnetic nanoparticle is made of ferric ferrous oxide ($Fe_3O_4$), and wherein the shell 12 is made of a conductive polymer containing multi-biofunctional groups, and wherein the conductive polymer is a polyaniline derivative, and wherein the multi-biofunctional group (R) is expressed by wherein R'=$CH_2CH_2$ or CH=CH, and wherein M=H, Li, Na, K, or $NH_4^+$.

A fluorescent label or an antibody can be attached to the multi-biofunctional groups of the shell 12. Therefore, the magnetic nanocomposites of the present invention can function as an intelligent MRI contrast agent or a medicine carrier.

Figure 2:
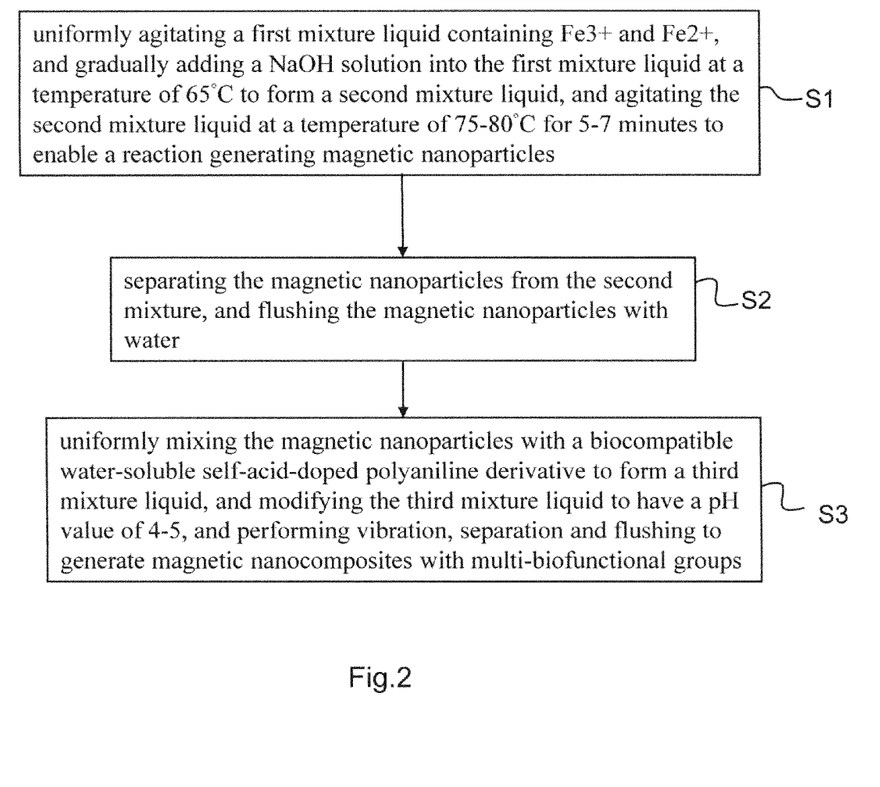
FIG. 2 is a flowchart of a method for fabricating a magnetic nanocomposite with multi-biofunctional groups according to the present invention.

Refer to FIG. 2 a flowchart of a method for fabricating a magnetic nanocomposite with multi-biofunctional groups according to the present invention. In Step S1, uniformly agitate a first mixture liquid containing ferric ion ($Fe^{3+}$) and ferrous ion ($Fe^{2+}$), and gradually add an aqueous solution of NaOH into the first mixture liquid at a temperature of 65° C. to form a second mixture liquid, and agitate the second mixture liquid at a temperature of 75-80° C. for 5-7 minutes to enable a reaction generating magnetic nanoparticles with a diameter of 5-10 nm, wherein the molar ratio of [$Fe^{3+}$]:[$Fe^{2+}$]:[NaOH] of the second mixture liquid=2:3:8. In Step S2, after the second mixture liquid cools down, separate the magnetic nanoparticles from the second mixture with a separating device, and flush the magnetic nanoparticles with water at least five times. In Step S3, uniformly mix the magnetic nanoparticles with a biocompatible water-soluble self-acid-doped polyaniline derivative to form a third mixture liquid; use 1 N HCl aqueous solution to modify the third mixture liquid to have a pH value of 4-5; vibrate the third mixture liquid with an ultrasonic oscillator at a temperature of 15-20° C. for 30 minutes to enable a reaction generating magnetic nanocomposites; separate the magnetic nanoparticles from the third mixture liquid with a separating device; flush the magnetic nanoparticles with deionized water at least five times to form magnetic nanocomposites having a diameter of 15-30 nm and containing multi-biofunctional groups, wherein the multi-biofunctional group is expressed by wherein R'=$CH_2CH_2$ or CH=CH, and wherein M=H, Li, Na, K, or $NH_4^+$.

The abovementioned separating device is a combination of a separating funnel and a strong permanent magnet. The contrast agent made of the magnetic nanocomposites has superparamagnetism and a maximum concentration of 0-25 mg/mL.

From the above description, it is found that the method of the present invention can fabricate magnetic nanocomposites containing multi-biofunctional groups in a simple, fast and low-cost way without using any surfactant or dispersant, wherein the magnetic nanocomposites a small size and disperse in water easily.

The abovementioned biocompatible water-soluble self-acid-doped polyaniline derivative has a structure expressed by Formula (I):

wherein 0<x<1, and wherein each of $R_1$, $R_2$, $R_3$, $R_4$ is selected from a group consisting of —H, —$CH_3$, —$C_2H_5$, —$C_3H_7$, —F, —Cl, —Br, —I, —$COR_7$, —$OCOR_7$, —$NO_2$, —$COOR_7$, and —CN, and wherein $R_7$ is a $C_1$-$C_8$ alkyl functional group, and wherein each of $R_5$ and $R_6$ is selected from a group consisting of —H, —$COR_8COOH$ and —$COR_8COO^-$, and wherein $R_8$ is a $C_2$-$C_4$ alkyl functional group or a $C_2$-$C_4$ alkenyl functional group.

The cyclic anhydride of the polyaniline derivative is selected from a group consisting of wherein n is 4, 8, 10, 14, or 18.

Below, the embodiments are described in detail to demonstrate the present invention.

Embodiment I Precipitation Method for Fabricating Magnetic $Fe_3O_4$ Nanoparticle (MNP)

Figure 5:
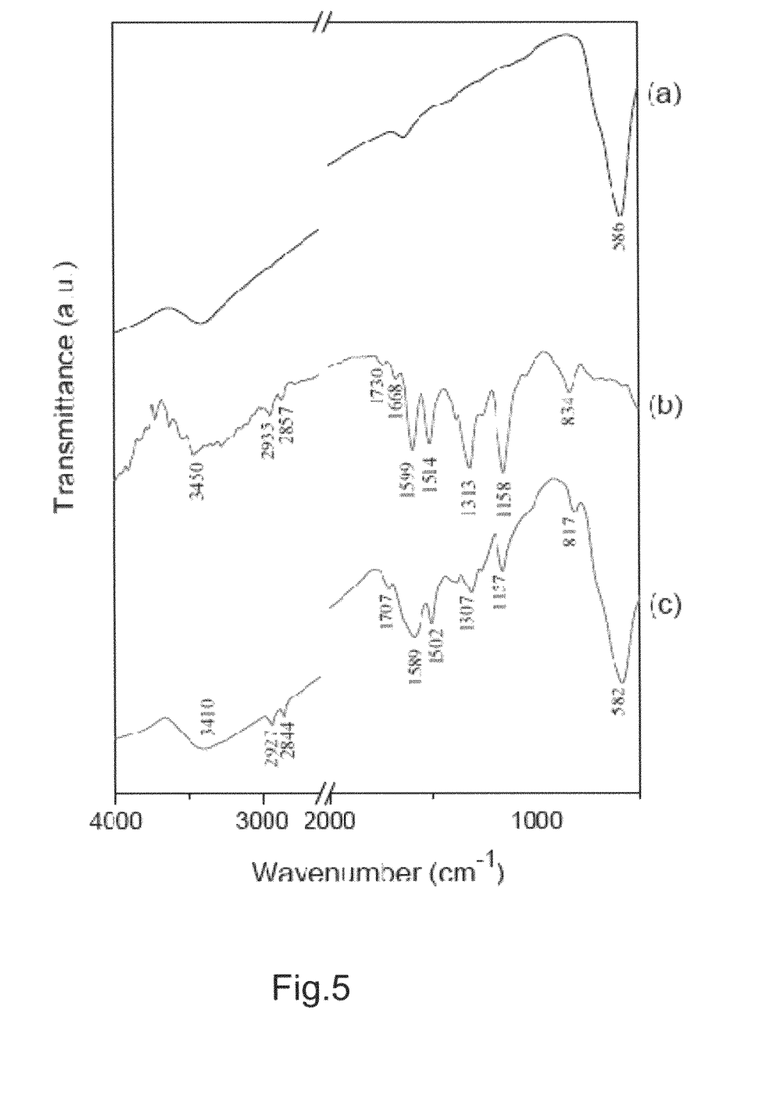
FIG. 5(a) is an FT-IR spectrum of MNP at an ambient temperature.
FIG. 5(b) is an FT-IR spectrum of SPAnNa at an ambient temperature.
FIG. 5(c) is an FT-IR spectrum of an MNP/SPAnH nanocomposite at an ambient temperature.
Figure 6:
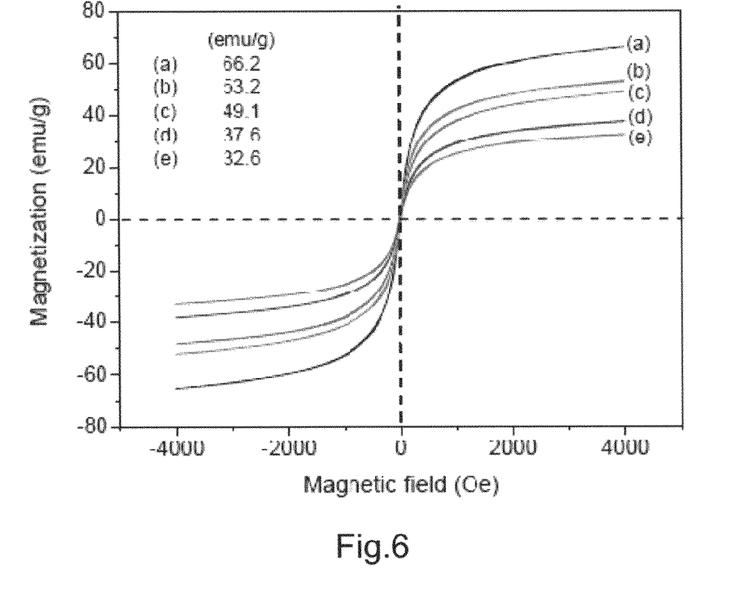
FIG. 6(a) is a magnetic hysteresis curve of MNP at an ambient temperature.
FIG. 6(b) is a magnetic hysteresis curve of an MNP/SPAnH nanocomposite containing 9.60 wt % of SPAnH at an ambient temperature.
FIG. 6(c) is a magnetic hysteresis curve of an MNP/SPAnH nanocomposite containing 9.99 wt % of SPAnH at an ambient temperature.
FIG. 6(d) is a magnetic hysteresis curve of an MNP/SPAnH nanocomposite containing 12.57 wt % of SPAnH at an ambient temperature.
FIG. 6(e) is a magnetic hysteresis curve of an MNP/SPAnH nanocomposite containing 16.45 wt % of SPAnH at an ambient temperature.

Firstly, 0.7 g ($4.32 \times 10^{-3}$ mole) $FeCl_3$, 1.07 g ($6.48 \times 10^{-3}$ mole) $FeCl_2.4H_2O$ and 400 ml of double distilled water are added into a three-necked bottle and agitated at an ambient temperature and in a nitrogen environment for 5 minutes to completely dissolve $FeCl_3$ and $FeCl_2.4H_2O$, Next, 20 mL of 0.864N NaOH aqueous solution is added into the three-necked bottle, and the temperature of the solution is raised to 80° C., whereby $Fe_3O_4$ MNPs are formed. Next, the reaction products are cooled down rapidly and vibrated with an ultrasonic vibrator to uniformly disperse the magnetic nanoparticles in the aqueous solution. Next, the mixture solution is poured into a separating funnel, and a strong magnet is placed outside the funnel to attract the magnetic nanoparticles with the solution flowing away from the bottom of the funnel, whereby the solution and the magnetic nanoparticles are separated. Next, double distilled water is used to flush the magnetic nanoparticles repeatedly until the solution is neutralized and colorless. From the TEM photograph in FIG. 3(a), it is observed that the MNPs have a particle size of about 8 nm. Curve (a) in FIG. 5 is an infrared spectrum of MNPs. The Fe—O ($v_{Fe-O}$) stretching vibration of MNPs appears at 586 $cm^{-1}$. Via SQUID (Superconducting Quantum Interference Device), the saturation magnetization of MNPs is found to be 66.2 emu/g. As shown in Curve (a) of FIG. 6, the saturation magnetization of MNPs increases with the magnetic field, and the magnetization curve passes through the origin, wherefore the MNPs of the present invention has the feature of superparamagnetism.

Embodiment II

Figure 4:
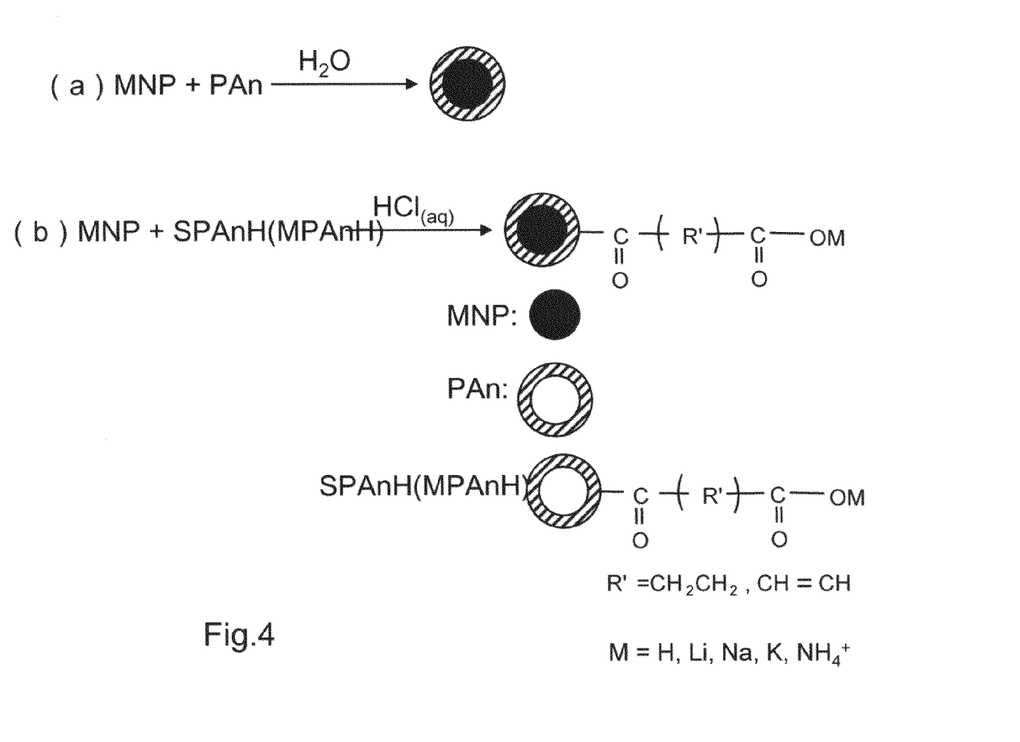
FIG. 4(a) is a diagram schematically showing the structure and the reaction process of the MNP/PAn nanocomposite.
FIG. 4(b) is a diagram schematically showing the structure and the reaction process of the MNP/SPAnH nanocomposite.

A DMSO solution of PAn (polyaniline) (0.41 mg/mL) is gradually dripped into an aqueous solution of MNPs (1.22 mg/Ml) at an ambient temperature. On contacting water, the PAn molecules aggregate and wrap MNPs to form magnetic nanocomposites with the core being MNPs and the shell being PAn. Next, the magnetic nanocomposites are separated from the solution and then dispersed in double distilled water. Thus are formed MNP/PAn nanocomposites. The structure and the reaction process of the MNP/PAn nanocomposite is schematically shown in FIG. 4(a).

Embodiment III

Firstly, 10 mL of an MNP aqueous solution (6.4 mg/mL) and 4 mL of an SPAnNa (poly[aniline-co-sodium N-(1-one-butyric acid)aniline]) aqueous solution (1.85 mg/mL) are mixed uniformly. The mixed solution is vibrated with an ultrasonic vibrator, and a 0.5M HCl solution is dropped into the mixed solution. In an acidic environment, SPAnNa aggregates and envelops the magnetic nanoparticles to form a magnetic nanocomposite with the core being MNPs and the shell being SPAnH (poly[N-(1-tone-butyric acid)]aniline). Next, the magnetic nanocomposites are separated from the solution and then dispersed in double distilled water. Thus are formed the MNP/SPAnH nanocomposites. The structure and the reaction process of the MNP/SPAnH nanocomposite is schematically shown in FIG. 4(b).

Curve (c) in FIG. 5 is an infrared spectrum of the MNP/SPAnH nanocomposites. In the infrared spectrum of the MNP/SPAnH nanocomposites, there is also a Fe—O ($v_{Fe-O}$) stretching vibration appearing at 582 $cm^{-1}$; there are a saturation-symmetric stretching vibration and a saturation-asymmetric stretching vibration of C—H ($v_{C-H}$) respectively appearing at 2844 $cm^{-1}$ and 2927 $cm^{-1}$; and there are a C=O ($v_{C=O}$) stretching vibration and an O—H ($v_{O-H}$) stretching vibration of the functional group —COOH respectively appearing at 1707 $cm^{-1}$ and 3410 $cm^{-1}$. The abovementioned stretching vibrations indicate that MNPs are indeed enveloped by a layer of SPAnH. From the SQUID measurement shown in Curve (b) of FIG. 6, it is found that the magnetic nanocomposite of the present invention has superparamagnetism with a saturation magnetization of 53.2 emu/g.

Embodiment IV

Firstly, 10 mL of an MNP aqueous solution (6.4 mg/mL) and 4 mL of an SPAnNa (poly[aniline-co-sodium N-(1-one-butyric acid)aniline]) aqueous solution (3.7 mg/mL) are mixed uniformly. The mixed solution is vibrated with an ultrasonic vibrator, and a 0.5M HCl solution is dropped into the mixed solution. In an acidic environment, SPAnNa aggregates and envelops the magnetic nanoparticles MNPs to form a magnetic nanocomposite with the core being MNPs and the shell being SPAnH (poly[N-(1-tone-butyric acid)]aniline). Next, the magnetic nanocomposites are separated from the solution and then dispersed in double distilled water. Thus are formed the MNP/SPAnH nanocomposites. The process is schematically shown in FIG. 4(a).

Curve (c) in FIG. 5 is an infrared spectrum of the MNP/SPAnH nanocomposites. In the infrared spectrum of the MNP/SPAnH nanocomposites, there is also a Fe—O ($v_{Fe-O}$) stretching vibration appearing at 582 cm$^{-1}$; there are a saturation-symmetric stretching vibration and a saturation-asymmetric stretching vibration of C—H ($v_{C-H}$) respectively appearing at 2844 cm$^{-1}$ and 2927 cm$^{-1}$; and there are a C=O ($v_{C=O}$) stretching vibration and an O—H ($v_{O-H}$) stretching vibration of the functional group —COOH respectively appearing at 1707 cm$^{-1}$ and 3410 cm$^{-1}$. The abovementioned stretching vibrations indicate that MNPs are indeed enveloped by a layer of SPAnH. From the SQUID measurement shown in Curve (e) of FIG. 6, it is found that the magnetic nanocomposite of the present invention has superparamagnetism with a saturation magnetization of 32.6 emu/g.

Embodiment V

Firstly, 10 mL of an MNP aqueous solution (6.4 mg/mL) and 4 mL of an SPAnNa (poly[aniline-co-sodium N-(1-one-butyric acid)aniline]) aqueous solution (4.9 mg/mL) are mixed uniformly. The mixed solution is vibrated with an ultrasonic vibrator, and a 0.5M HCl solution is dropped into the mixed solution. In an acidic environment, SPAnNa aggregates and envelops the magnetic nanoparticles MNPs to form a magnetic nanocomposite with the core being MNPs and the shell being SPAnH. Next, the magnetic nanocomposites are separated from the solution and then dispersed in double distilled water. Thus are formed the MNP/SPAnH nanocomposites. The process is schematically shown in FIG. 4(a).

Figure 3:
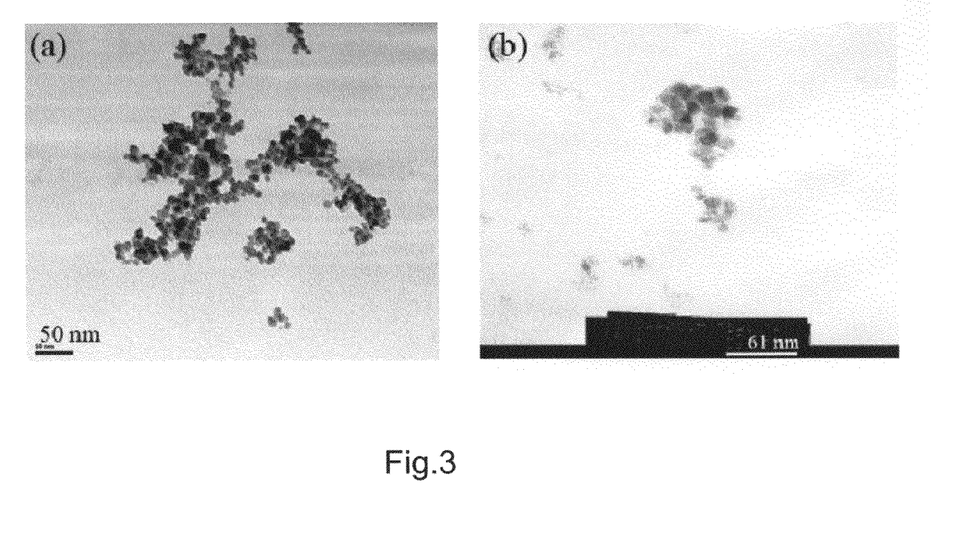
FIG. 3(a) is a TEM photograph of MNP.
FIG. 3(b) is a TEM photograph of MNP/SPAnH.

From the TEM photograph in FIG. 3(b), it is observed that the MNPs have a particle size of about 18 nm. Curve (c) in FIG. 5 is an infrared spectrum of MNP/SPAnH nanocomposites. The Fe—O ($v_{Fe-O}$) stretching vibration of MNPs appears at 582 cm$^{-1}$; there are a saturation-symmetric stretching vibration and a saturation-asymmetric stretching vibration of C—H ($v_{V-H}$) respectively appearing at 2844 cm$^{-1}$ and 2927 cm$^{-1}$; and there are a C=O ($v_{C=O}$) stretching vibration and an O—H ($v_{O-H}$) stretching vibration of the functional group —COOH respectively appearing at 1707 cm$^{-1}$ and 3410 cm$^{-1}$. The abovementioned stretching vibrations indicate that MNPs are indeed enveloped by a layer of SPAnH. From the SQUID measurement shown in Curve (d) of FIG. 6, it is found that the magnetic nanocomposite of the present invention has superparamagnetism with a saturation magnetization of 37.6 emu/g.

Embodiment VI

Firstly, 10 mL of an MNP aqueous solution (6.4 mg/mL) and 4 mL of an SPAnNa (poly[aniline-co-sodium N-(1-one-butyric acid)aniline]) aqueous solution (7.4 mg/mL) are mixed uniformly. The mixed solution is vibrated with an ultrasonic vibrator, and a 0.5M HCl solution is dropped into the mixed solution. In an acidic environment, SPAnNa aggregates and envelops the magnetic nanoparticles MNPs to form a magnetic nanocomposite with the core being MNPs and the shell being SPAnH. Next, the magnetic nanocomposites are separated from the solution and then dispersed in double distilled water. Thus are formed the MNP/SPAnH nanocomposites. The process is schematically shown in FIG. 4(a).

Curve (c) in FIG. 5 is an infrared spectrum of the MNP/SPAnH nanocomposites. In the infrared spectrum of the MNP/SPAnH nanocomposites, there is also a Fe—O ($v_{Fe-O}$) stretching vibration appearing at 582 cm$^{-1}$; there are a saturation-symmetric stretching vibration and a saturation-asymmetric stretching vibration of C—H ($v_{C-H}$) respectively appearing at 2844 cm$^{-1}$ and 2927 cm$^{-1}$; and there are a C=O ($v_{C=O}$) stretching vibration and an O—H ($v_{O-H}$) stretching vibration of the functional group —COOH respectively appearing at 1707 cm$^{-1}$ and 3410 cm$^{-1}$. The abovementioned stretching vibrations indicate that MNPs are indeed enveloped by a layer of SPAnH. From the SQUID measurement shown in Curve (c) of FIG. 6, it is found that the magnetic nanocomposite of the present invention has superparamagnetism with a saturation magnetization of 49.1 emu/g.

Embodiment VII

Firstly, 150 μL of a liquid containing 10000 HUVEC (Human Umbilical Vein Endothelial Cell) is placed in each well of 96-well culture plates, wherein the wells are coated with a 1% gelatin solution. Next, the culture plates are placed in a humidified incubator at a temperature of 37 C.° and with 5% $CO_2$ to enable adherent growth of the cells. 24 hours later, 50 μL of a MNP solution is added into each well, wherein the MNPs are dispersed in an M199 medium to form the abovementioned MNP solution, and wherein the MNP solution has a concentration of 25, 50, 100, or 150 μg/mL. Next, the culture plates are placed in a humidified incubator at a temperature of 37 C.° and with 5% $CO_2$ once again. 24 hours later, observe the cell growth and count the cells. Remove the M199 medium beforehand, and add 120 μL of a reaction liquid XTT (2,3-Bis(2-methoxy-4-nitro-5-sulfophenyl)-2H-tetrazolium-5-carboxanilide inner salt) to the cells. Use an ELISA reader (BIO-TEK, model EL 808) to measure the OD value at 499 nm to evaluate the biotoxicity of MNP.

Figure 7:
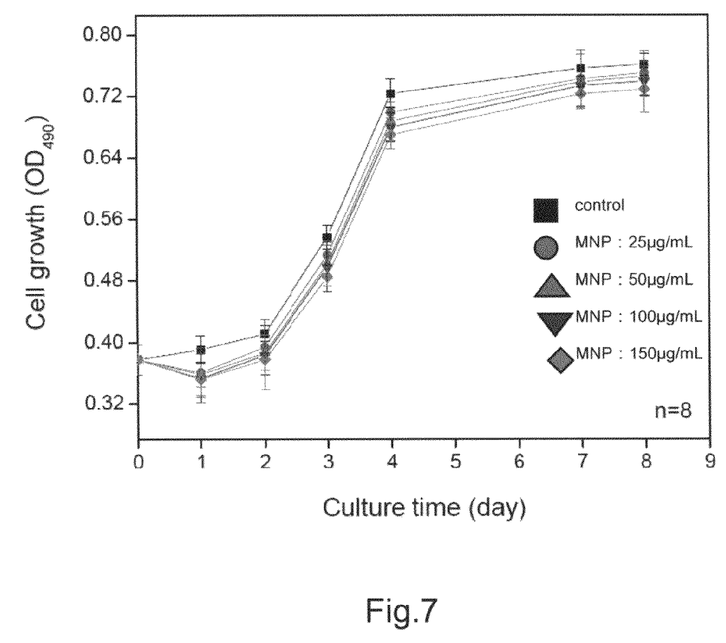
FIG. 7 shows the relationship between the mitochondrion activity of HUVEC and the culture time, wherein HUVEC is cultured for 1-8 days in environments of 25-150 µg/mL MNP solutions, and wherein HUVEC cultured in an MNP-free environment functions as a control group.

FIG. 7 shows the relationship between the mitochondrion activity of HUVEC and the culture time, wherein HUVEC is cultured for 1-8 days in environments of 25-150 μg/mL MNP solutions, and wherein HUVEC cultured in an MNP-free environment functions as a control group. In the first day, the number of HUVEC in the environments of MNP is less than that in the control group, and the number of cells decreases obviously with the concentrations of MNP. It may be attributed the fact that MNP denatures the culture medium. Thus, some cells cannot adapt to the denatured culture medium and gradually separate from the substrate. However, the residual cells begin to adapt to the environments and grow adherently in the second day. From the second day to the fourth day, the cells grow exponentially. At the fast-growth stage, the cells divide and increase rapidly. From the fourth day to the eighth day, the cell growth slows down. In the fast-growth stage of from the second day to the fourth day, the cell growth rates in the MNP environments and the cell growth rate in the MNP-free environment are undifferentiated. Therefore, the biotoxicity of MNP is unobvious in the abovementioned concentration range (Refer to Table. 1).

Embodiment VIII

Firstly, 150 μL of a liquid containing 10000 HUVEC (Human Umbilical Vein Endothelial Cell) is placed in each well of 96-well culture plates, wherein the wells are coated with a 1% gelatin solution. Next, the culture plates are placed in a humidified incubator at a temperature of 37 C.° and with 5% $CO_2$ to enable adherent growth of the cells. 24 hours later, 50 μL of a MNP/SPAnH nanocomposite solution is added into each well, wherein the MNP/SPAnH nanocomposite is dispersed in an M199 medium to form the abovementioned MNP/SPAnH nanocomposite solution, and wherein the MNP/SPAnH nanocomposite solution has a concentration of 25, 50, 100, or 150 m/mL. Next, the culture plates are placed in a humidified incubator at a temperature of 37 C.° and with 5% $CO_2$ once again. 24 hours later, observe the cell growth and count the cells. Remove the M199 medium beforehand, and add 120 μL of a reaction liquid XTT to the cells. Next, cultivate the cells in incubators for 3 hours. Next, take 100 μL of the XTT solution where the reaction has occurred from each well. Use an ELISA reader (BIO-TEK, model EL 808) to measure the OD value at 499 nm to evaluate the biotoxicity of MNP/SPAnH.

Figure 8:
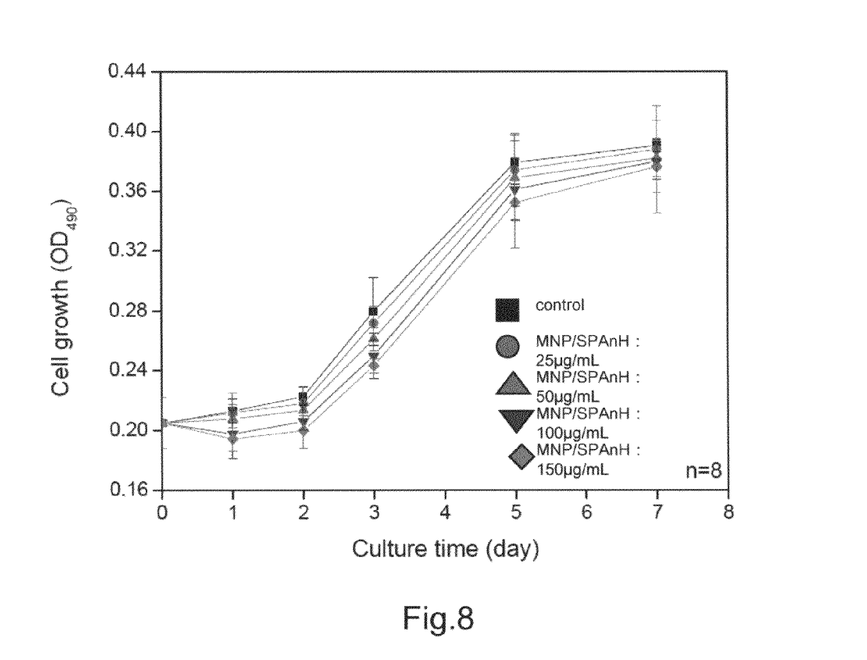
FIG. 8 shows the relationship between the mitochondrion activity of HUVEC and the culture time, wherein HUVEC is cultured for 1-7 days in environments of 25-150 µg/mL MNP/SPAnH solutions, and wherein HUVEC cultured in an MNP/SPAnH-free environment functions as a control group.

FIG. 8 shows the relationship between the mitochondrion activity of HUVEC and the culture time, wherein HUVEC is cultured for 1-7 days in environments of 25-150 μg/mL MNP/SPAnH solutions, and wherein HUVEC cultured in an MNP/SPAnH-free environment functions as a control group. In the first day, the number of HUVEC in the environments of MNP/SPAnH is less than that in the control group, and the number of cells decreases obviously with the concentrations of MNP/SPAnH. It may be attributed the fact that MNP/SPAnH denatures the culture medium. Thus, some cells cannot adapt to the denatured culture medium and gradually separate from the substrate. However, the residual cells begin to adapt to the environments and grow adherently in the second day. From the second day to the fifth day, the cells grow exponentially. At the fast-growth stage, the cells divide and increase rapidly. From the fifth day to the seventh day, the cell growth slows down. In the fast-growth stage of from the second day to the fifth day, the cell growth rates in the MNP/SPAnH environments and the cell growth rate in the MNP/SPAnH-free environment are undifferentiated. Therefore, the biotoxicity of MNP/SPAnH is unobvious in the abovementioned concentration range (Refer to Table. 1).

TABLE 1

| | Concentration ($\mu gmL^{-1}$)/growth rate ($\times 10^{-3}$, $h^{-1}$) | | | | |
|---|---|---|---|---|---|
| MNP | 0/6.51 | 25/6.35 | 50/6.26 | 100/6.16 | 150/6.07 |
| MNP/SPAnH | 0/2.18 | 25/2.17 | 50/2.16 | 100/2.15 | 150/2.12 |
| MNP/MPAnH | 0/2.04 | 25/2.04 | 50/2.01 | 100/1.99 | 150/1.97 |

Embodiment IX

Firstly, 2 mL of a liquid containing 20000 HUVEC (Human Umbilical Vein Endothelial Cell) is placed in culture dishes, wherein the culture dishes are coated with a 1% gelatin solution. Next, the culture dishes are placed in a humidified incubator at a temperature of 37 C.° and with 5% $CO_2$ to enable adherent growth of the cells. 24 hours later, 100 μL of a MNP/SPAnH nanocomposite solution is added into the culture dishes, wherein the MNP/SPAnH nanocomposite is dispersed in an M199 medium to form the abovementioned MNP/SPAnH nanocomposite solution. 24 hours later, flush the contents of the culture dishes with 1 mL of HBSS (Hanks' Balance Slat Solution). Next, use a live/dead dye to dye the cells. Next, flush the dyed cells with HBSS. Then, observe the cell growth status with a confocal microscope (Leica Germany, model TCS SP2).

Figure 9:
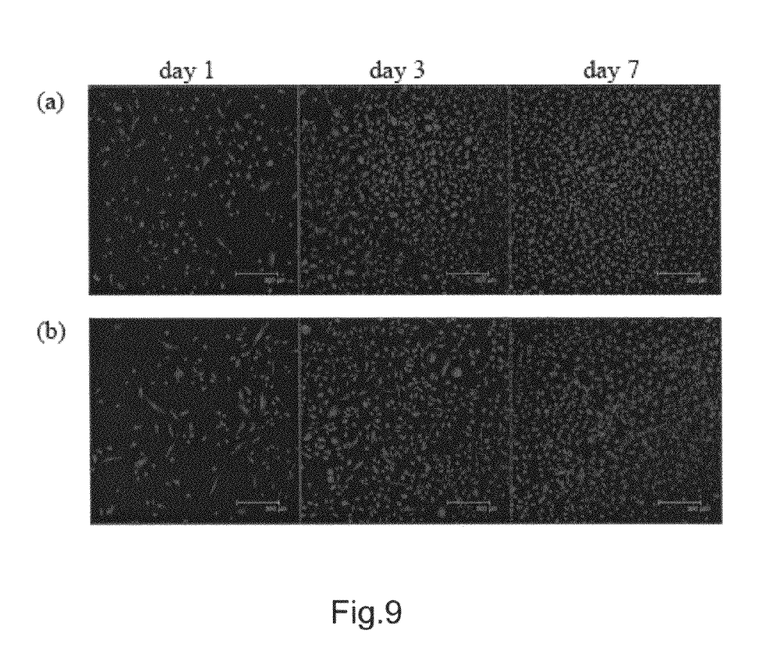
FIG. 9 shows the fluorescent images of HUVEC cultivated for 1-7 days in the MNP/SPAnH-free environment (the control group) and the MNP/SPAnH environment (150 µg/mL)

FIG. 9 shows the fluorescent images of HUVEC cultivated for 1-7 days in the MNP/SPAnH-free environment (the control group) and the MNP/SPAnH environment (150 μg/mL). In the first day, the cells in the MNP/SPAnH environment are less than the cells in the control group. However, the cells in the MNP/SPAnH environment increase with time and have the same growth tendency as the cells in the control group. Such a result meets the cell growth curves and indicates that the MNP/SPAnH nanocomposite is non-biotoxic.

Embodiment X

Firstly, 10 mL of an MNP aqueous solution (6.4 mg/mL) and 4 mL of an MPAnNa (Poly[N-(sodium-1-one-2-vinyl-butyrate)]aniline) aqueous solution (3.7 mg/mL) are mixed uniformly. The mixed solution is vibrated with an ultrasonic vibrator, and a 0.5M HCl solution is dropped into the mixed solution. In an acidic environment, MPAnNa aggregates and envelops the magnetic nanoparticles MNPs to form a magnetic nanocomposite with the core being MNPs and the shell being MPAnH (Poly[N-(1-one-2-vinyl-butyric acid)]aniline). Next, the magnetic nanocomposites are separated from the solution, flushed with double distilled water until the flushing water becomes neutral, and then dispersed in double distilled water. Thus are formed the MNP/MPAnH nanocomposites. The process is schematically shown in FIG. 4(a).

Next, 150 μL of a liquid containing 10000 HUVEC is placed in each well of 96-well culture plates, wherein the wells are coated with a 1% gelatin solution. Next, the culture plates are placed in a humidified incubator at a temperature of 37 C.° and with 5% $CO_2$ to enable adherent growth of the cells. 24 hours later, 50 μL of an MNP/MPAnH solution is added into each well, wherein the MNP/MPAnH nanocomposites are dispersed in an M199 medium to form the abovementioned MNP/MPAnH solution, and wherein the MNP/MPAnH solution has a concentration of 25, 50, 100, or 150 μg/mL. Next, the culture plates are placed in a humidified incubator at a temperature of 37 C.° and with 5% $CO_2$ once again. 24 hours later, observe the cell growth and count the cells. Remove the M199 medium beforehand, and add 120 μL of a reaction liquid XTT to the cells. Use an ELISA reader (BIO-TEK, model EL 808) to measure the OD value at 499 nm to evaluate the biotoxicity of MNP/MPAnH.

Figure 10:
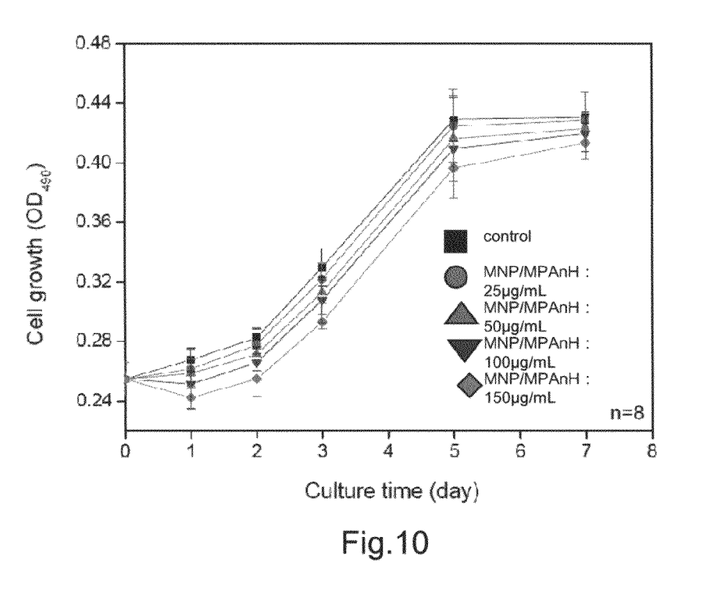
FIG. 10 shows the relationship between the mitochondrion activity of HUVEC and the culture time, wherein HUVEC is cultured for 1-7 days in environments of 25-150 µg/mL MNP/MPAnH solutions, and wherein HUVEC cultured in an MNP/MPAnH-free environment functions as a control group.

FIG. 10 shows the relationship between the mitochondrion activity of HUVEC and the culture time, wherein HUVEC is cultured for 1-7 days in environments of 25-150 μg/mL MNP/MPAnH solutions, and wherein HUVEC cultured in an MNP/MPAnH-free environment functions as a control group. In the first day, the number of HUVEC in the environments of MNP/MPAnH is less than that in the control group, and the number of cells decreases obviously with the concentrations of MNP/MPAnH. It may be attributed the fact that MNP/MPAnH denatures the culture medium. Thus, some cells cannot adapt to the denatured culture medium and gradually separate from the substrate. However, the residual cells begin to adapt to the environments and grow adherently in the second day. From the second day to the fifth day, the cells grow exponentially. At the fast-growth stage, the cells divide and increase rapidly. From the fifth day to the seventh day, the cell growth slows down. In the fast-growth stage of from the second day to the fifth day, the cell growth rates in the MNP/MPAnH environments and the cell growth rate in the MNP/

MPAnH-free environment are undifferentiated. Therefore, the biotoxicity of MNP/MPAnH is unobvious in the above-mentioned concentration range (Refer to Table. 1).

Embodiment XI

Figure 11:
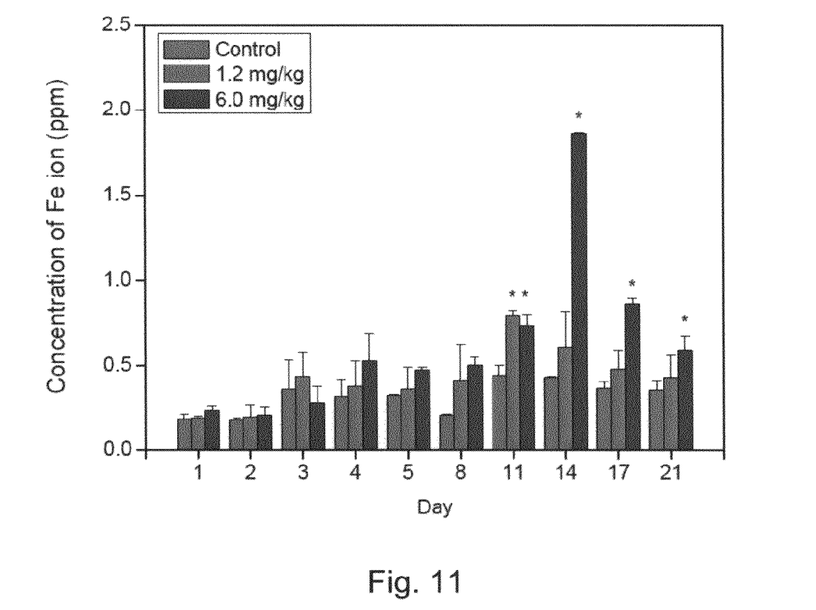
FIG. 11 shows the result of urine analysis.
Figure 12:
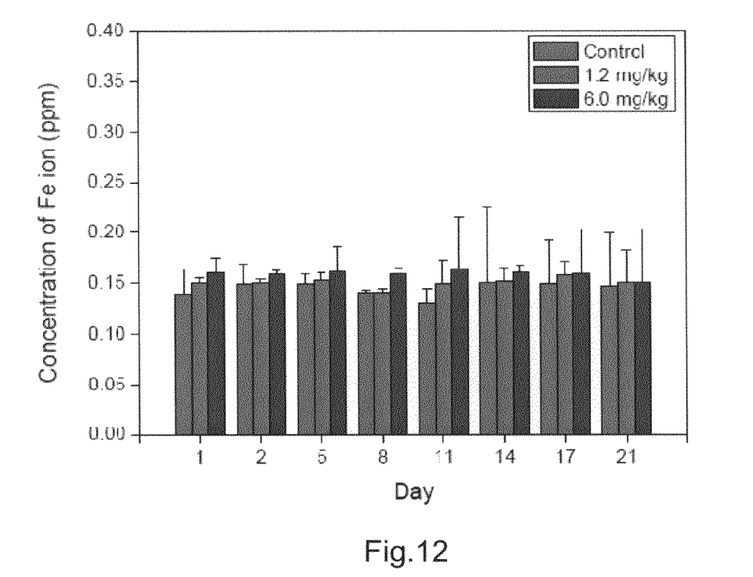
FIG. 12 shows the result of excrement analysis.

To understand the metabolism of the contrast agent made of the magnetic nanocomposite (MNP/SPAnH nanocomposite) of the present invention, the MNP/SPAnH nanocomposite is injected into the bodies of mice by doses of 1.2 mg/kg and 6 mg/kg to form an experimental group. The mice without injection are used as a control group. Each group is triplicate. Collect the urine and excrement of the mice everyday for 21 days. Add a 12M hydrochloric acid solution to the urine to dissolve the iron ion of the MNP/SPAnH nanocomposite. Use ICP-OES (Induced Couple Plasma Optical Emission Spectrometry) to detect the concentration of the iron ion in the urine, whereby is learned the excretion of the MNP/SPAnH nanocomposite via urine. From FIG. 11, it is known that the iron content of the urine of the experimental group is obviously higher that that of the control group from the eleventh day to the fourteenth day after the injection of the MNP/SPAnH nanocomposite. The MNP/SPAnH nanocomposite is metabolized into a water-soluble product by the liver, and water-soluble product is metabolized into urine by the kidney. The total iron amounts detected in urine are respectively 83% and 69% of the iron amounts injected into the mice bodies. Therefore, most of the contrast agent is excreted via urine, and only a small amount of the contrast agent remains in the body. The collected excrement is baked and then ground into powder. Next, dissolve the excrement powder with 12M aqua regia. Next, use ICP-OES to detect the concentration of the iron ion in the excrement, whereby is learned the excretion of the MNP/SPAnH nanocomposite via excrement. From FIG. 11, it is known that the iron content of the excrement of the experimental group is indifferent to that of the control group in the 21 days since the injection of the MNP/SPAnH nanocomposite. Therefore, the liver does not metabolize the MNP/SPAnH nanocomposite into a fat-soluble product, and the MNP/SPAnH nanocomposite would not be excreted via the intestines.

Embodiment XII

Figure 13:
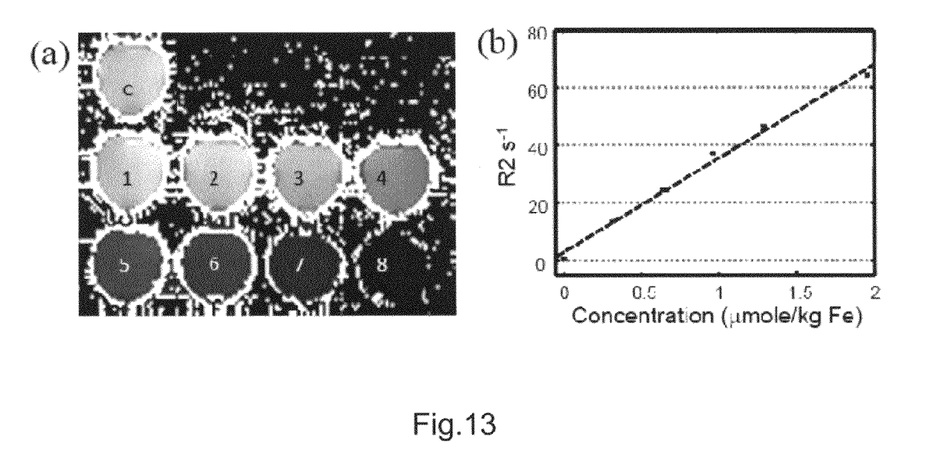
FIG. 13 shows the MRI images of the samples containing different concentrations of MNP/SPAnH.

In a 24-well plate, make up the standard samples of magnetic nanocomposite gel with a 1% gelatin solution and the magnetic nanocomposite (MNP/SPAnH) solutions respectively with concentrations of 0.32, 0.648, 0.96, 1.292, 1.96, 3.2, 4.8 and 6.48 μmole/kg. The samples free of the MNP/SPAnH nanocomposite are used as the control group. Use a 3-T magnetic resonance imager to detect the spin-spin relaxation rates (R2) and determine the concentrations of iron. From FIG. 13($a$), it is known that the signal intensity increases with the concentration of iron. From FIG. 13($b$), it is known that R2 increases with the concentration of iron. These phenomena are attributed to the fact that the gradient of the magnetic field in the magnetic nanocomposite gel increase with the concentration of iron. The relationship between R2 and the concentration of iron is linear within the concentration range of 0-1.96 μmole/kg with the slope being 32.39 second$^{-1}$ μmole/kg$^{-1}$. Such a relationship can be applied to quantify the MRI contrast agent inside the animal body.

Embodiment XIII

All the animal experiments were approved by the institutional animal care and use committee. All the mice in the experiments are male Sprague-Dawley mice weighing 250±50 g. The anesthetic is a mixture of ketamine (40 mg/kg) and xylazine (10 mg/kg). The anesthetic is given via intravenous injection. Divide the mice into two groups. The MNP/SPAnH nanocomposite is respectively injected into the bodies of the two groups of mice by doses of 15 μmole/kg and 150 μmole/kg. In each of the first day, the seventh day, the fourteenth day and the twenty-first day after injection, three mice are sacrificed. The livers, spleens, hearts, lungs and kidneys of the mice are taken out, flushed with saline, dried with a vacuum oven, and ground into powder. Next, dissolve the powder with 12N aqua regia. Then, use ICE-OES to detect the concentrations of iron of the solutions.

Embodiment XIV

Figure 14:
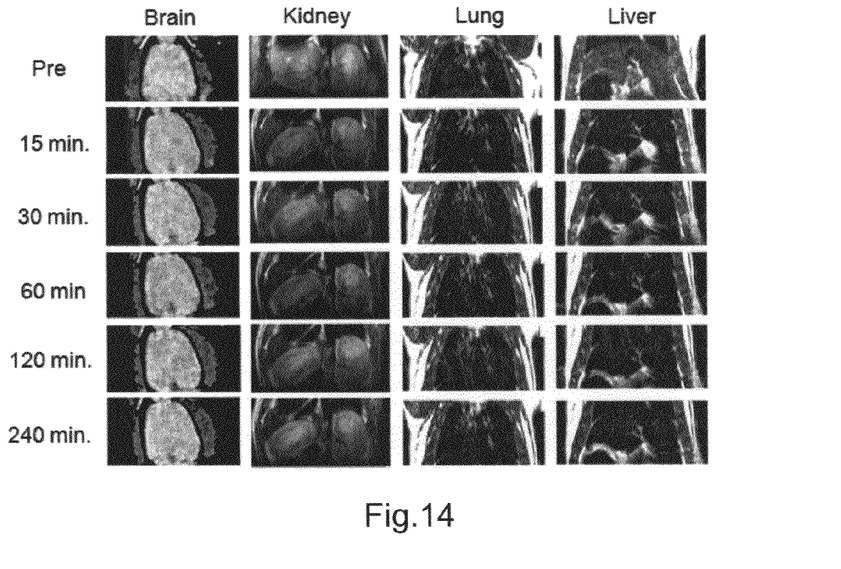
FIG. 14 shows the MRI images of the organs accumulating different amounts of MNP/SPAnH.
Figure 15:
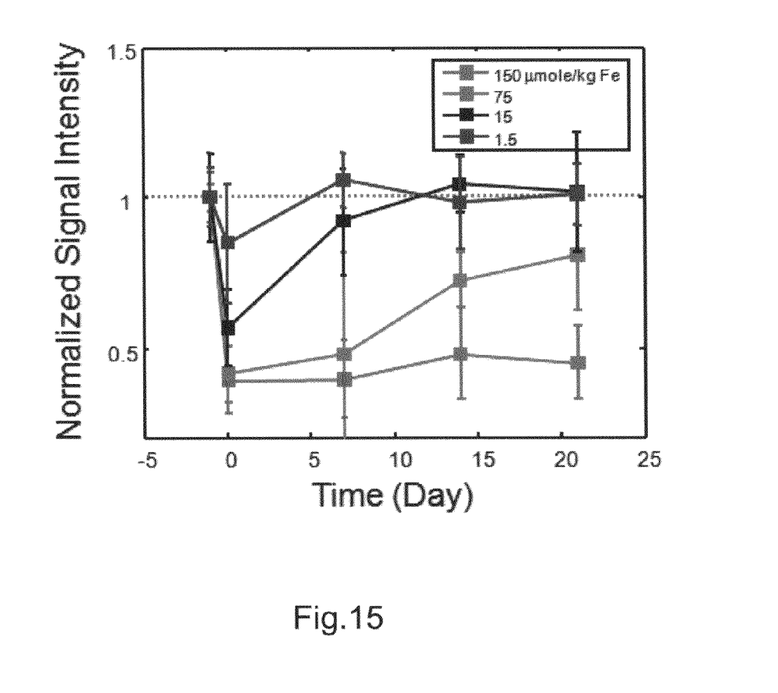
FIG. 15 shows that the MNP/SPAnH concentrations vary with time in livers under different doses of MNP/SPAnH injections.

Inject the MNP/SPAnH nanocomposite solution into the bodies of mice via the caudal veins by doses of 1.5 mole/kg (n=3), 15 μmole/kg (n=3), 75 μmole/kg (n=3), and 150 μmole/kg (n=3). Within four hours since injection, use MRI T2 images to observe the distributions of the IVfNP/SPAnH nanocomposite (15 mole/kg) in the brains, kidneys, lungs and livers. The parameters of the T2 images include TR/TE=2000 ms/102 ms, slice thickness=1.5 mm, matrix size=194×320, FOV=68×100 mm and voxel size of 0.35×0.31×1.5 mm$^3$. FIG. 14 shows the MRI T2 images within four hours since injection. The T2 images indicate that the MNP/SPAnH nanocomposite does not accumulates in brains, lungs and kidneys but accumulates in livers with time. Use MRI T2 images to observe the distribution of the MNP/SPAnH nanocomposite in livers in the thirtieth minute, the seventh day, the fourteenth day, and the twenty-first day after the injection. Use the intensities of the T2 image signals to work out the signal-to-noise ratios (SNR). Refer to FIG. 15. The SNR. values of the images of livers has decreased respectively by 10%, 45%, 60%, and 60% in the fifteenth minute after injecting the MNP/SPAnH nanocomposite by doses of 1.5 μmole/kg, 15 μmole/kg, 75 μmole/kg, and 150 μmole/kg. The more the SNR value of the liver image decreases, the higher the concentration of iron in the liver is. In the seventh day after the injection by a dose of 1.5 μmole/kg, SNR has been 100% restored. In the fourteenth day after the injection by a dose of 15 μmole/kg, SNR has been 100% restored. In the case of a dose of 75 μmole/kg, SNR is only 70% restored in the fourteenth day after the injection. In the case of a dose of 150 mole/kg, SNR still remains the same even in the twenty-first day after the injection. Therefore, the higher the concentration of injection is, the longer the time the liver requires to metabolize the magnetic nanocomposite. Such a result matches the result of the experiment of urine. A portion of the MNP/SPAnH nanocomposite will be metalized by the liver into a water-soluble product and excreted via urine.

The embodiments described above are only to exemplify the present invention but not to limit the scope of the present invention. Any equivalent modification or variation according to the characteristics and spirit of the present invention is to be also included within the scope of the present invention.

What is claimed is:
1. A magnetic nanocomposite with multi-biofunctional groups, comprising
   a core formed of magnetic nanoparticles; and
   a shell wrapping said core and made of a polyaniline derivative conductive polymer with multi-biofunctional groups, wherein said polyaniline derivative conductive polymer has a structure expressed by Formula (I):

wherein 0<x<1;
wherein each of $R_1$, $R_2$, $R_3$, $R_4$ is selected from a group consisting of —H, —$CH_3$, —$C_2H_5$, —$C_3H_7$, —F, —Cl, —Br, —I, —$COR_7$, —$OCOR_7$, —$COOR_7$, and —CN; $R_7$ is a $C_1$-$C_8$ alkyl functional group; and
each of $R_5$ and $R_6$ is said multi-biofunctional group expressed as the following structure wherein R'=$CH_2CH_2$ or CH=CH, and
wherein M=H, Li, Na, K, or $NH_4^+$.

2. The magnetic nanocomposite with multi-biofunctional groups according to claim 1, which applies to a medicine carrier or a contrast agent.

3. The magnetic nanocomposite with multi-biofunctional groups according to claim 1, wherein a solution of said magnetic nanocomposite having a maximum concentration of 0-25 mg/mL is used in a magnetic resonance imaging contrast agent.

4. The magnetic nanocomposite with multi-biofunctional groups according to claim 1, which has a diameter of 15-30 nm.

5. The magnetic nanocomposite with multi-biofunctional groups according to claim 1, which has superparamagnetism.

6. The magnetic nanocomposite with multi-biofunctional groups according to claim 1, wherein said magnetic nanoparticle is made of ferric ferrous oxide ($Fe_3O_4$).

7. A method for fabricating the magnetic nanocomposite with multibiofunctional groups of claim 1, comprising steps:
uniformly agitating a first mixture liquid containing ferric ion and ferrous iron, and adding a basic solution into said first mixture liquid to form a second mixture liquid containing a plurality of magnetic nanoparticles;
separating said magnetic nanoparticles from said second mixture liquid; and
uniformly mixing said magnetic nanoparticles with the biocompatible water-soluble self-acid-doped polyaniline derivative to form a third mixture liquid, using an acidic solution to modify said third mixture liquid to have a pH value of 4-5, oscillating said third mixture liquid to enable a reaction generating a plurality of magnetic nanocomposites, and separating said magnetic nanocomposites from said third mixture liquid to obtain magnetic nanocomposites with multi-biofunctional groups.

8. The method for fabricating a magnetic nanocomposite with multi-biofunctional groups according to claim 7, wherein said basic solution is a solution of sodium hydroxide (NaOH).

9. The method for fabricating a magnetic nanocomposite with multi-biofunctional groups according to claim 8, wherein a molar ratio of ferric ion, ferrous ion and sodium hydroxide in said second mixture liquid ($[Fe^{3+}]$:$[Fe^{2+}]$:[NaOH]) is 2:3:8.

10. The method for fabricating a magnetic nanocomposite with multi-biofunctional groups according to claim 7, wherein said basic solution is added into said first mixture liquid having a temperature of 65° C.

11. The method for fabricating a magnetic nanocomposite with multi-biofunctional groups according to claim 7, wherein said second mixture liquid is agitated for 5-7 minutes at a temperature of 75-80° C.

12. The method for fabricating a magnetic nanocomposite with multi-biofunctional groups according to claim 7 further comprising a step of flushing said magnetic nanoparticles with deionized water after said magnetic nanoparticles are separated from said second mixture liquid.

13. The method for fabricating a magnetic nanocomposite with multi-biofunctional groups according to claim 7, wherein said acidic solution is hydrochloric acid.

14. The method for fabricating a magnetic nanocomposite with multi-biofunctional groups according to claim 7, wherein said biocompatible water-soluble self-acid-doped polyaniline derivative is expressed by wherein 0<x<1, and
wherein each of $R_1$, $R_2$, $R_3$, $R_4$ is selected from a group consisting of —H, —$CH_3$, —$C_2H_5$, —$C_3H_7$, —F, —Cl, —Br, —I, —$COR_7$, —$OCOR_7$, —$NO_2$, —$COOR_7$, and —CN, and
wherein $R_7$ is a $C_1$-$C_8$ alkyl functional group, and
wherein each of $R_5$ and $R_6$ is selected from a group consisting of —H, —$COR_8COOH$ and —$COR_8COO^-$, and
wherein $R_8$ is a $C_2$-$C_4$ alkyl functional group or a $C_2$-$C_4$ alkenyl functional group.

15. The method for fabricating a magnetic nanocomposite with multi-biofunctional groups according to claim 14, wherein a cyclic anhydride used in said polyaniline derivative is selected from a group consisting of —CH=CHCH$_2$(CH$_2$)$_n$CH$_3$, wherein n is 4, 8, 10, 14, or 18.

16. The method for fabricating a magnetic nanocomposite with multi-biofunctional groups according to claim 7, wherein said third mixture liquid is oscillated to enable a reaction for 30 minutes at a temperature of 15-20° C.

17. The method for fabricating a magnetic nanocomposite with multi-biofunctional groups according to claim 7, wherein said magnetic nanoparticles are separated from said second mixture liquid with a separating device containing a separating funnel and a string permanent magnet.

18. The method for fabricating a magnetic nanocomposite with multi-biofunctional groups according to claim 7, wherein said magnetic nanoparticles having a diameter of 5-10 nm.

19. The method for fabricating a magnetic nanocomposite with multi-biofunctional groups according to claim 7, wherein said magnetic nanocomposites having a diameter of 15-30 nm.

20. The method for fabricating a magnetic nanocomposite with multi-biofunctional groups according to claim 7 further comprising a step of flushing said magnetic nanocomposites with deionized water after said magnetic nanocomposites are separated from said third mixture liquid.

21. The method for fabricating a magnetic nanocomposite with multi-biofunctional groups according to claim 7, wherein said magnetic nanocomposites are separated from said third mixture liquid with a separating device containing a separating funnel and a string permanent magnet.

22. The method for fabricating a magnetic nanocomposite with multi-biofunctional groups according to claim 7, wherein said multi-biofunctional group is wherein R'=CH$_2$CH$_2$ or CH=CH, and
wherein M=H, Li, Na, K, or NH$_4^+$.

23. The method for fabricating a magnetic nanocomposite with multi-biofunctional groups according to claim 7, wherein said magnetic nanocomposites have superparamagnetism.

24. The method for fabricating a magnetic nanocomposite with multi-biofunctional groups according to claim 7, wherein said magnetic nanocomposites apply to a medicine carrier or a contrast agent.

* * * * *

UNITED STATES PATENT AND TRADEMARK OFFICE
CERTIFICATE OF CORRECTION

PATENT NO. : 8,974,769 B2  Page 1 of 1
APPLICATION NO. : 12/799893
DATED : March 10, 2015
INVENTOR(S) : Mu-Yi Hua It is certified that error appears in the above-identified patent and that said Letters Patent is hereby corrected as shown below:

On the title page item 75

The inventors should be listed as Mu-Yi Hua, Tao-Yuan, (TW); Hao-Li Liu, Tao-Yuan, (TW); Hung-Wei Yang, Tao-Yuan, (TW); Rung-Ywan Tsai, Kaohsiung City, (TW); Kuo-Chen Wei, Taipei City, (TW); Pin-Yuan Chen, Taipei City, (TW)

Signed and Sealed this
Twenty-fourth Day of November, 2015

Michelle K. Lee
*Director of the United States Patent and Trademark Office*